US00RE37555E

(19) United States
(12) Reissued Patent
Ackerman et al.

(10) Patent Number: US RE37,555 E
(45) Date of Reissued Patent: Feb. 19, 2002

(54) PROCESS AND COMPOSITION FOR MULTICOMPONENT ONE HUNDRED PERCENT SOLID FABRIC SOFTENERS

(75) Inventors: Jeannene A. Ackerman, Trumbull, CT (US); Michael Miller, Bexley, OH (US); David E. Whittlinger, Janesville, WI (US)

(73) Assignee: Goldschmidt Chemical Company, Hopewell, VA (US)

(21) Appl. No.: 09/330,621

(22) Filed: Jun. 11, 1999

Related U.S. Patent Documents

Reissue of:
(64) Patent No.: 5,221,794
Issued: Jun. 22, 1993
Appl. No.: 07/793,216
Filed: Nov. 7, 1991

U.S. Applications:

(63) Continuation of application No. 07/472,738, filed on Jan. 31, 1990, now abandoned.

(51) Int. Cl.[7] ..... C07C 209/00; C07D 233/24

(52) U.S. Cl. ..... 510/330; 510/331; 510/491; 510/500; 510/505; 510/515; 510/520; 544/1; 544/52; 544/103; 544/223; 564/204; 564/205; 564/215; 564/291; 564/292; 564/294; 564/296

(58) Field of Search ..... 548/349.1; 554/1, 554/52, 103, 223; 564/204, 215, 291, 292, 294, 296; 510/330, 331, 491, 500, 505, 515, 519, 520

(56) References Cited

U.S. PATENT DOCUMENTS

| | | | | |
|---|---|---|---|---|
| 2,474,202 | A | 6/1949 | Rust | 260/404.5 Q |
| 2,583,772 | A | 1/1952 | Gunderson | 260/404.5 Q |
| 3,686,025 | A | 8/1972 | Morton | 252/8.8 |
| 3,936,537 | A | 2/1976 | Baskerville, Jr. et al. | 427/242 |
| 4,022,938 | A | 5/1977 | Zaki et al. | 427/242 |
| 4,237,064 | A | 12/1980 | Reck | 260/459 A |
| 4,238,373 | A | 12/1980 | Hardy et al. | 252/542 |
| 4,832,856 | A | 5/1989 | Rutzen | 252/8.8 |
| 4,844,824 | A | 7/1989 | Mermelstein et al. | 252/8.75 |
| 4,851,141 | A | 7/1989 | Demangeon et al. | 252/8.75 |
| 4,857,213 | A | 8/1989 | Caswell et al. | 252/8.75 |
| 4,859,456 | A | 8/1989 | Marschner | 424/47 |

FOREIGN PATENT DOCUMENTS

| | | |
|---|---|---|
| EP | 0048163 | 3/1982 |
| EP | 0345475 | 12/1989 |
| EP | 0 345 495 A2 | 12/1989 |

*Primary Examiner*—Richard L. Raymond
(74) *Attorney, Agent, or Firm*—Scully, Scott, Murphy & Presser

(57) ABSTRACT

The invention relates to a method of producing a mixture of a quaternary ammonium compound, fatty acid, fatty acid ester and tertiary amine salt in situ which is a highly functional mixture that is manufactured in a single step reaction whereby quaternization is completed without the aid of solvents, especially flammable solvents. The single step reaction process eliminates separate blending of individual components. The compositions obtained can be used as fabric softeners, in modified clays, as hair treating compounds and as disinfectants.

17 Claims, No Drawings

PROCESS AND COMPOSITION FOR MULTICOMPONENT ONE HUNDRED PERCENT SOLID FABRIC SOFTENERS

Matter enclosed in heavy brackets [ ] appears in the original patent but forms no part of this reissue specification; matter printed in italics indicates the additions made by reissue.

This application *is a reissue application of U.S. application Ser. No. 793,216, filed Nov. 7, 1991, now U.S. Pat. No. 5,221,794, which in turn* is a continuation of application Ser. No. 472,738, filed on Jan. 31, 1990, now abandoned.

BACKGROUND OF THE INVENTION

1. Field of the Invention

The invention relates to a method of producing a mixture of a quaternary ammonium compound, fatty acid, fatty acid ester and tertiary amine salt in situ which is a highly functional mixture that is manufactured in a single step reaction whereby quaternization is completed without the aid of solvents, especially flammable solvents. The single step reaction process eliminates separate blending of individual components.

2. Brief Description of the Prior Art

The preparation of quaternary ammonium compounds is usually conducted in stainless steel or glass-lined equipment to which a tertiary amine is charged and a solvent. Flammable solvents such as isopropyl alcohol are generally used although mixtures of isopropyl alcohol and water sometimes are employed or water alone is used. Flammable solvents are also undesirable because they are a fire hazard and special handling procedures are required when they are used. In many applications, these solvents have to be stripped from the mixture when the reaction is completed because the ultimate use of the product is in a solventless or solid form.

After the reactants are loaded into the reactor they are heated to a temperature of about 50 to about 100° C. after which a quaternizing reagent is added. In some instances an exotherm is produced as a result of the quaternizing reaction and the reactor and its contents have to be cooled. The rate of addition of the quaternizing agent can also be controlled in order to minimize or eliminate the exotherm. As noted previously, in some instances, the solvent, if any is employed in the quaternizing reaction is stripped from the quaternary ammonium compound obtained since some commercial uses for the compounds are in solventless systems. Additionally, bulk shipments of quaternary ammonium compounds with solvents adds to transportion costs which is another reason to remove the solvents.

The largest use for quaternary ammonium compounds is as a fabric softener and presently accounts for more than about three quarters of the total market for these material. Some fabric softeners are supplied as a liquid dispersion of from about 3% to about 10% by weight of the quaternary ammonium compound which is adapted to be added during the rinse cycle of a commercial or home laundering operation. Another significant fabric softening application is the utilization of quaternary ammonium compounds in combination with a substrate such as a nonwoven fabric or a polymeric foam such as a polyurethane foam, this substrate so treated being added to a fabric dryer such as a clothes dryer while the fabric or clothes are still damp. The quaternary ammonium compound is formulated usually with a fatty acid ester which promotes the transfer of the quaternary ammonium compound from the nonwoven or porous polymeric substrate to the fabric or clothes.

Lastly, quaternary ammonium compounds are now being added to both solid and liquid laundry detergent compositions so that the quaternary ammonium compound can be incorporated as a fabric softener during the wash cycle of fabrics or clothes. The most successfully utilized quaternary ammonium compounds in this last respect are the dimethyl (dihydrogenated tallow) ammonium chlorides or methyl sulfates. Other quaternary ammonium compounds such as imidazolines and amidoamine quaternaries are also used in this regard.

Where the quaternary ammonium compound is used on a substrate for transfer to fabric or clothing in a fabric or clothes dryer, it has generally been the practice to separately blend the fatty acid ester into the quaternary ammonium compound which involves the extra manufacturing steps of transportion, handling and blending of the fatty acid esters into the quaternary ammonium compounds. If these steps can be eliminated a cost savings could be realized.

Quaternary ammonium compounds are also used to manufacture organomodified clays which may be added to drilling muds utilized in drilling oil wells, the organomodified clay providing improved lubrication and rheological properties of the drilling muds. These organoclays are also employed as thixotropic agents in plastisols, organosols, paints and other protective coatings, grease additives, foundry additives, cosmetics, resins and printing inks. The most common quaternary ammonium compounds employed in this regard are methyldi(hydrogenated tallow) benzylammonium chloride, dimethyldi(hydrogenated tallow) ammonium chloride and dimethyl(hydrogenated tallow) benzylammonium chloride.

Quaternary ammonium compounds are also employed as bactericides the most common of which is the quaternary ammonium compound of benzylchloride and a dimethylalkylamine, the alkyl group having from about 12 to about 16 carbon atoms as well as trimethyl alkyl ammonium chlorides where the alkyl group is a long chain alkyl such as an octadecyl group. Additionally, dimethyldicoconut-oil fatty ammonium chlorides are also effective disinfectants e.g. bactericides or bacteristats, especially against anaerobic bacteria which are sulfate reducers that are found in oil wells, these bacteria causing severe corrosion problems and plugging of formations which this type of quaternary ammonium compound can minimize or eliminate. Additionally, these quaternary ammonium compounds effective against anaerobic bacteria are also effective in removing oil from sand stone formations in oil wells and provide a two-fold effect or functioning not only as a bactericide but also in promoting so-called secondary recovery of oil.

An additional use of quaternary compounds is in hair treatment because of the antistatic effects obtained with such compounds, as well as the increased wetting which promotes improvements in both wet and dry combing or brushing and improves luster and feel. The most commonly used quaternary ammonium compounds in this respect are trimethylalkylammonium chloride, pentaethoxystearylammonium chloride, dimethylstearylbenzylammonium chloride and dimethyldialkylammonium chlorides.

It is therefore an object to overcome these and other difficulties encountered in the prior art.

It is also an object of the present invention to provide a method for manufacturing a mixture of quaternary ammonium compounds with a fatty ester inter allia which can be used in fabric softening applications. It is also an object of the present invention to provide such mixtures.

It is a further object of the invention to provide mixtures of quaternary ammonium compounds with fatty acid esters, amine salts and fatty acids that can be employed in any or all of the foregoing applications.

These and other objects have been achieved according to the present invention which will be further understood in view of the following description and claims.

SUMMARY OF THE INVENTION

It has been found that a highly functional mixture of a quaternary ammonium compound, a fatty acid ester, an ammonium salt and a fatty acid can be obtained in a single step reaction without the aid of solvents, especially flammable solvents to thereby produce a mixture of highly functional components. The single step reaction thereby eliminates the separate blending of such individual components as the fatty acid ester, the ammonium salt and the fatty acid with the quaternary ammonium compound.

The advantage of the method of the present invention is that it provides a composition that is non-flammable and it is ready to be flaked or powdered because of its bulk form and can be used as a fabric softener, a fabric lubricant, a hair condition as well as an anti-static agent that can be released from a substrate such as a nonwoven fabric or a polymeric foam. These mixtures can also be used in combination with synthetic detergents or as lubricant, an emulsifier, in cosmetic preparations hair conditioning components clay modifiers, bactericidal compositions and as a floculant.

DETAILED DESCRIPTION

As noted, the invention relates to a method for producing a quaternary ammonium mixture that is highly functional by means of a single step reaction as well as the various compositions that can be obtained thereby and therewith.

In its broadest aspect the invention is directed to a method of producing a mixture of a quaternary ammonium compound, fatty acid, fatty acid ester and tertiary amine salt by reacting a tertiary amine, quaternizing agent and fatty acid, each in amount so that said mixture will contain at least a quaternary ammonium compound, a fatty acid, fatty acid ester and a tertiary amine salt. The tertiary amine employed according to the invention has the formula:

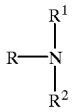

where R, $R^1$ and $R^2$ can be any of the following in any combination.

(1) linear or branched chain saturated or unsaturated hydrocarbon groups having up to about 22 carbon atoms;

(2) a lower hydroxy alkyl group;

(3) an alkyl amido alkylene group of the formula:

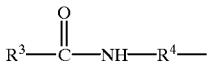

where $R^4$ is lower alkylene and $R^3$ is any of R, $R^1$ or $R^2$;

(4) lower alkoxy group;

(5) poly(oxyloweralkylene) group; so that at least one of R, $R^1$ or $R^2$ is one of said linear or branched chain aliphatic saturated or unsaturated hydrocarbon groups;

or said tertiary amine is an imidazoline of the formula:

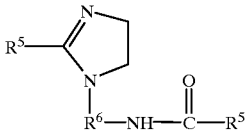

where $R^5$ is a linear or branched chain, aliphatic saturated or unsaturated hydrocarbon group having up to about 22 carbon atoms and $R^6$ is a lower alkylene group;

said quaternizing agent being known in the art and which will produce a quaternary ammonium compound having an anion $A^-$. Generally these quaternizing agents are those having the formula $R^7_{(a-b)}X$;

where $R^7$ is a lower alkyl group or cyclo lower alkyl group such as benzyl, cyclohexylmethyl, tolyl, xylyl, naphthylmethyl, and X may be a chlorine, iodine, bromine, sulfate, methyl sulfate, carbonate, phosphate, borate group, formate, acetate, propionate, adipate, benzoate and the like where (a) is equal to the valence of X and (b) is from 1 to the valence of X.

said fatty acid is a linear or branched chain aliphatic saturated or unsaturated fatty acid having from about 12 to about 22 carbon atoms based on coconut oil, vegetable oils, seed oils animal fats and fish oils;

Various tertiary amines that can be employed in this regard include dimethylamino propyl amine, amino ethylanolamine, distearly methyl amine, dihydrogenated tallow methyl amine, ditallow methyl amine, dimethyl hydrogenated tallow amine, dimethyl coco amine, distearyl ethoxyethyl amine, stearyl bis-hydroxyethyl amine, stearyl bis (polyethoxy ethanol) amine, bis (tallowamidoethyl) 2-hydroxyethyl amine, bis (tallowamidoethyl) 2-hydroxylpropyl amine, 1-hydrogenated tallow amido ethyl -2-hydrogenated tallow imidazoline 1-ethylene bis (2tallow, 1-methyl, imidazolinium) dimethyl amino propyl tallow amidoamine and hydrogenated tallow hydroxyethyl imidazoline

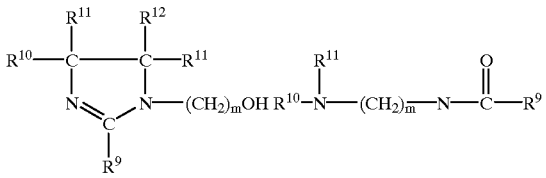

where $R^9$, $R^{10}$, $R^{11}$ and $R^{12}$ are subsequently defined.

The prior art also disclosed other amines that may be used such as those described in the U.S. Patents to Marschner, U.S. Pat. No. 4,859,456; Caswell et al., U.S. Pat. No. 4,857,213; Demangeon, U.S. Pat. No. 4,851,141 and Mermelstein et al., U.S. Pat. No. 4,844,824 all of which are incorporated by reference (also referred to hereafter as "the prior art cited herein.")

Imidazoline compounds that may be used are also described in Demangeon (supra), whereas the quarternizing agents include;

dimethyl sulfate, diethyl sulfate, methyl chloride, methyl bromide and benzyl chloride as well as those cited in the prior art cited herein.

The quaternary ammonium compound thus obtained has the formula:

(I)

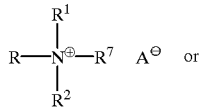

(II)

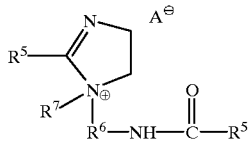

where R, $R^1$, $R^2$, $R^3$, $R^4$, $R^5$, $R^6$ and $R^7$ have been defined above;

where $A^-$ is an anion based on $R^7_{(a-b)}X$ or equivalent anions known in the quaternary ammonium compound art;

(III)

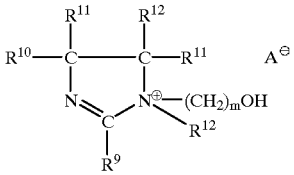

where $R^9$ is about C8 to C30, preferably about C12 to about C18 alkyl or [akenyls] *alkenyl*

$R^{10}$ and $R^{11}$ are independently hydrogen or C1 to about C4 alkyl $R^{12}$ is C1 to about C4 alkyl m is about 2 to about 3

$A^-$ is preferably an anion such as chloride, bromide, sulfate, methosulfate, nitrite, phosphate and carbosylate (i.e., acetate, adipate, propionate, benzoate)

(IV)

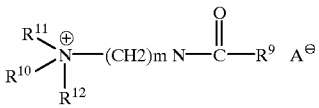

where $R^9$, $R^{10}$, $R^{12}$, m and $A^-$ have been previously defined.

The tertiary amine salt has the formula:

(V)

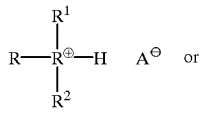

(VI)

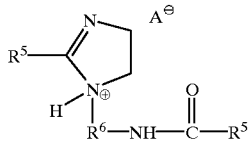

-continued

VII

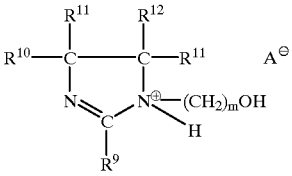

VIII

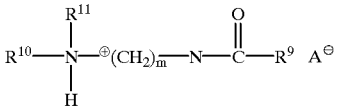

and the fatty acid ester has the formula:

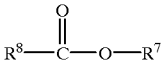

wherein $R^8$ is a linear or a branched chain aliphatic saturated or unsaturated hydrocarbon group having from about 11 to about 21 carbon atoms.

As used throughout this specification the terms lower alkoxy, lower alkylene and lower alkyl are intended to include compounds having up to about 3 or about 4 carbon atoms including the various isomeric configurations thereof e.g. t-butyl, i-butyl, i-propyl and the like and the various mixtures thereof whether such mixtures of such groups contain components having one, or two, or three or four carbon atoms or more and also where such groups individually or in combination are in any of their isomeric forms.

In another embodiment, according to the method of the invention the tertiary amine, quaternizing agent and fatty acid are reacted with one another each in an amount so that the mixture obtained contains from about 10 weight percent to about 80 weight percent and especially from about 35 weight percent to about 55 weight percent of said quaternary ammonium compound, about 15 weight percent to about 70 weight percent and especially from about 10 weight percent to about 30 weight percent of said salt, about 1 weight percent to about 70 weight percent and especially from about 5 weight percent to about 25 weight percent of said ester and from about 5 weight percent to about 70 weight percent and especially from about 15 weight percent to about 35 weight percent of said fatty acid wherein the ratio of said quaternary ammonium compound to said salt is from about 2:1 to about 1:2.

In one embodiment, the method of the invention is preferably practiced so that the quaternary ammonium compound that is obtained has the structural formula (I) wherein at least one of R, $R^1$ and $R^2$ is a branched chain or linear aliphatic saturated or unsaturated hydrocarbon group having from about 12 to about 22 carbon atoms, preferably saturated, and especially those based on hard tallow acids (i.e. hydrogenated tallow fatty acids) and the balance, if any of the aforesaid R, $R^1$ and $R^2$ groups is a lower alkyl group and $R^7$ is a lower alkyl group. In another embodiment X is a sulfate group.

The invention also relates to a mixture of the various quaternary ammonium compounds as described above in combination with the various fatty acid esters, fatty acids, and tertiary amine salts also as described previously and in the amounts and ratios as described previously.

The invention also relates to a fabric softening article of manufacture comprising a fabric softening amount of any of the mixtures as described herein operatively associated with a substrate that will release such mixture to a fabric under fabric softening conditions encountered in a fabric or clothes dryer and includes the use of any of the aforesaid mixtures in a fabric softening relationship with a nonwoven or woven fiber or a polymeric open-celled or substantially open-celled foam substrate, such combination being prepared in a manner well known in the art. The mixture is employed in an amount from about 0.1 to about 10 gms and especially 1 to about 39 grms per 9 in. by 11 in. sheet.

The various polymeric foams that are employed in this respect comprise polyurethane foams as well as any of the art known equivalent foams.

Additionally, the invention is directed to a fabric cleaning composition comprising a detergent in combination with a fabric softening amount of any of the mixtures described herein. These detergents can be any of the art known anionic, cationic, nonionic or amphoteric synthetic detergents or wetting agents that are well known in the art or a soap i.e. the reaction product of a fatty acid with a alkaline hydroxide that is water soluble e.g. fatty acid reaction products of sodium, potassium or ammonium hydroxides or amines or the art known equivalents thereof.

These surfactants are further described in Kirk-Othmer, Encyclopedia of Chemical Technology, 3rd Edition Vol. 22 pp. 332–432 which is incorporated herein by reference. Some specific detergents that are especially suitable in this regard include:

Detergents that can be employed in this respect comprise alkyl benzene sulfate, sodium lauryl ether sulfate nonyl phenyl ethoxylates and alkyl alcohol ethoxylates as well as those noted in the prior art cited.herein.

The mixture of the invention is incorporated into the detergents (whether solid or liquid) by blending in a manner well known in the art. The amount of the mixture employed is any where from about 1 to about 50 and especially from about 2 to about 30 wt. % based on the quaternary ammonium compound and the active components of the detergent i.e. the component of the detergent that has both organophilic and hydrophilic groups.

The following example is illustrative.

The method of the invention as well as a mixture obtained according to this method is examplified by the preparation of a mixture employing the following components in the indicated amounts.

| Components | M.W. | Moles | % by Wt. |
|---|---|---|---|
| Dihydrogenated Tallow-Methyl-Amine | 523 | 1.00 | 56.63 |
| Stearic Acid | | | 30.00 |
| Dimethyl Sulfate | 126 | 0.98 | 13.37 |

The amine was charged to a clean, dry reactor which was heated to 140° F. A slight nitrogen purge was employed over the amine that was charged to prevent it from coming into contact with any air that might enter into the reactor during the reaction. The stearic acid was then charged, mixed and heated to 140° F. after which the dimethyl sulfate was charged in increments sufficient to maintain the temperature of the reaction mixture at 140–170° F. The reaction is exothermic and the end point of the reaction is indicated to some degree when an exotherm is no longer obtained. When the reaction was completed, the resultant mixture was allowed to cool. The foregoing method produced a reaction mixture which was analyzed by NMR analysis showing that the mixture obtained had the following components:

| | % |
|---|---|
| Quaternary Ammonium compound | 46 |
| Fatty Acid | 22 |
| Tertiary Amine and Amine Salt | 19 |
| Methyl Ester | 13 |

Although the invention has been described by reference to some embodiments, it is not intended that the novel method or the mixture obtained thereby as well as the fabric softening article of manufacture and the detergent containing a fabric softening amount of the mixture be limited thereby but that certain embodiments are intended being included as falling within the broad scope and spirit of the foregoing disclosure and the following claims.

We claim:

1. A method of producing a mixture of quaternary ammonium compound, fatty acid, fatty acid ester, and tertiary amine salt by reacting in a solvent free system, a tertiary amine, quaternizing agent, and fatty acid each in an amount so that said mixture will contain at least a quaternary ammonium compound, fatty acid, fatty acid ester and tertiary amine salt, wherein said tertiary amine has the formula:

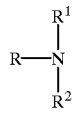

wherein R, $R^1$ or $R^2$ are:

(1) a linear or branched chain aliphatic saturated or unsaturated hydrocarbon group having up to about 22 carbon atoms;

(2) a hydroxy lower alkyl group;

(3) an alkyl amide alkylene group of the formula;

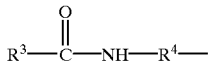

where $R^4$ is lower alkylene and wherein $R^3$ is (1), (2), (4) or (5);

(4) a lower alkoxy group;

(5) a poly(oxyloweralkylene) group; so that at least one of R, $R^1$ and $R^2$ is one of said hydrocarbon groups or one of said hydroxy lower alkyl groups;

or said tertiary amine is an imidazoline of the formula;

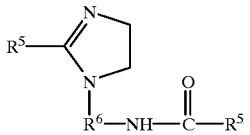

wherein $R^5$ is a linear or branched chain aliphatic saturated or unsaturated hydrocarbon group having up to about 22 carbon atoms and $R^6$ is a lower alkylene group, said quaternizing agent [being] *is* capable of producing a quaternary ammonium compound having anions $A^-$;

said fatty acid is a linear or branched chain saturated or unsaturated fatty acid having from about 12 to about 22 carbon atoms;

said quaternary ammonium compound [having] *has* the formula:

(I)

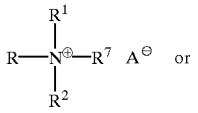

(II)

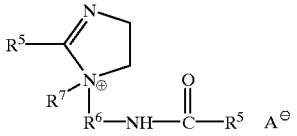

*wherein $R^7$ is a lower alkyl group or cyclo lower alkyl group;*

[and] *or* the salts of (I) and (II) [wherein R— is hydrogen;] *said tertiary amine salt has the formula;*

(V)

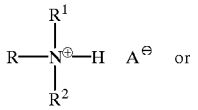

(VI)

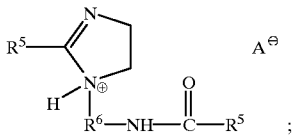

;

said fatty acid ester [having] *has* the formula:

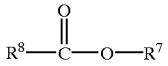

wherein $R^8$ is a linear or branched chain, aliphatic saturated or unsaturated hydrocarbon group having from about 11 to about 21 carbon atoms*;*

*and* where said tertiary amine, quaternizing agent and fatty acid are reacted with one another in an amount so that said mixture obtained contains about 10 wt. % to about 80 wt. % of said quaternary ammonium compound, about 15 wt. % to about 70 wt. % of said *tertiary amine* salt, about 1 wt. % to about 70 wt. % of said ester and about 5 wt. % to about 70 wt. % of said fatty acid [wherein] *and* the ratio of said quaternary ammonium compound to said *tertiary amine* salt is from about 2:1 to about 1:2 on a weight basis.

2. [The] *A* method of [claim 1 where said] *producing a mixture of quaternary ammonium compound, fatty acid, fatty acid ester, and tertiary amine salt by reacting in a solvent free system, a tertiary amine, quaternizing agent, and fatty acid each in an amount so that said mixture will contain at least a quaternary ammonium compound, fatty acid, fatty acid ester and tertiary amine salt, wherein* said *tertiary* amine is an imidazoline having the formula:

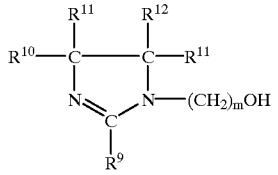

or is an amine of the formula:

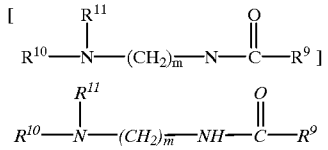

*where*

*$R^9$ is alkyl or alkenyl having about 8 to about 30 carbon atoms;*

*$R^{10}$ and $R^{11}$ are independently hydrogen or alkyl having up to about 4 carbon atoms; and*

*$R^{12}$ is alkyl having up to about 4 carbon atoms, said quaternizing agent is capable of producing a quaternary ammonium compound having anions $A^-$;*

*said fatty acid is a linear or branched chain saturated or unsaturated fatty acid having from about 12 to about 22 carbon atoms;*

[and] said quaternary ammonium compound has the formula:

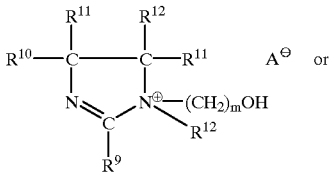

(III)

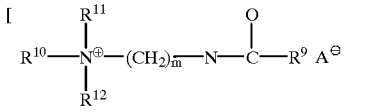

(IV) ]

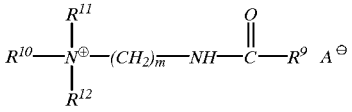

*(IV)*

[where $R^9$ is alkyl or akenyls having about 8 to about 30 carbon atoms;

$R^{10}$ and $R^{11}$ are independently hydrogen or alkyl having up to about 4 carbon atoms;

$R^{12}$ is alkyl having up to about 4 carbon atoms; and the salts of (III) or (IV) where $R^{12}$ on the nitrogen atom is hydrogen]

*and said tertiary amine salt has the formula:*

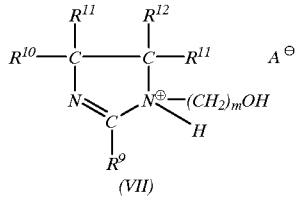

(VII)

*or*

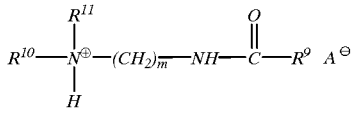

(VIII)

*and wherein said tertiary amine, quaternizing agent and fatty acid are reacted with one another in an amount so that said mixture obtained contains about 10 wt. % to about 80 wt. % of said quaternary ammonium compound, about 15 wt. % to about 70 wt. % of said tertiary amine salt, about 1 wt. % to about 70 wt. % of said ester and about 5 wt. % to about 70 wt. % of said fatty acid and the ratio of said quaternary ammonium compound to said tertiary amine salt is from about 2:1 to about 1:2 on a weight basis.*

3. The method of any of claims 1 or 2 where said tertiary amine, quaternizing agent and fatty acid are reacted with one another in an amount so that said mixture obtained contains about 35 wt. % to about 55 wt. % of said quaternary ammonium compound, about 10 wt. % to about 30 wt. % of said *tertiary amine* salt, about 5 wt. % to about 25 wt. % of said ester and about 15 wt. % to about 35 wt. % of said fatty acid [wherein the ratio of said quaternary ammonium compound to said salt is from about 2:1 to about 1:2 on a weight basis].

4. The method of claim 1 where said quaternary ammonium compound is *a compound of formula* (I) [or] wherein *at least one of the* R, $R^1$ and $R^2$ groups is a branched chain or linear, aliphatic saturated or unsaturated hydrocarbon group having from about 12 to about 22 carbon atoms and the balance, if any, of said R, $R^1$ and $R^2$ groups is a lower alkyl group.

5. The method of claim 4 where A is a lower alkyl sulfate group[;] and where *said at least one of the* R, $R^1$ and $R^2$ *groups* is [said] *a saturated* hydrocarbon group[, it is saturated].

6. As a composition of matter, a solvent free mixture of a quaternary ammonium compound having the formula:

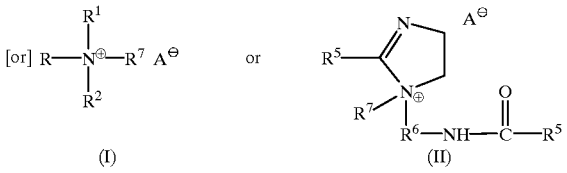

(I) (II)

where R, $R^1$ and $R^2$ are (1) linear or branched chain aliphatic saturated or unsaturated hydrocarbon group having up to about 22 carbon atoms;

(2) a hydroxy lower alkyl group;

(3) an alkyl amido alkylene group of the formula,

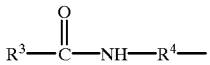

where $R^4$ is lower alkylene and $R^3$ is any of R, $R^1$ or $R^2$;

(4) a lower alkoxy group;

(5) a poly(oxyloweralkylene) group; so that at least one of R, $R^1$ or $R^2$ is one of said hydrocarbon groups or one of said hydroxy lower alkyl groups, where $R^5$ is a linear or branched chain aliphatic saturated or unsaturated hydrocarbon group having up to about 22 carbon atoms [and], $R^6$ is a lower alkylene group,

*$R^7$ is lower alkyl group or cyclo lower alkyl group, and* [where]

$A^-$ is an anion;

a linear or branched chain saturated or unsaturated fatty acid having from about 12 to about 22 carbon atoms;

a tertiary amine salt having *the* formula [(I) or (II) where $R^7$ is hydrogen];

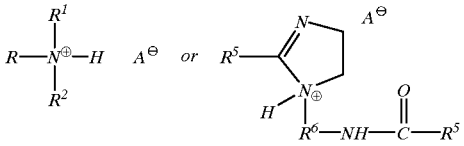

and a fatty acid ester having the formula:

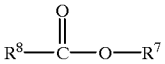

where $R^8$ is a linear or branched chain, aliphatic saturated or unsaturated group having from about 11 to about 21 carbon atoms.

7. [The] *As a* composition of [claim 6 where said amine is an imidazoline having the formula] *matter, a solvent free mixture of a quaternary ammonium compound having the formula:*[

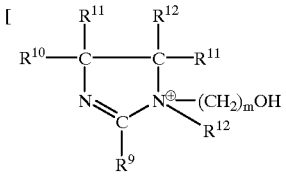

or an amine of the formula:

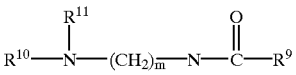

said quaternary ammonium compound has the formula]

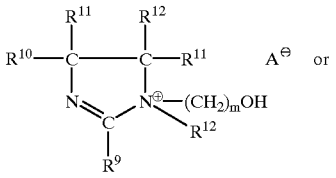

(III)

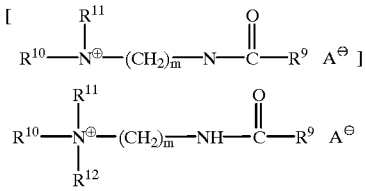

(IV)

where $R^9$ is alkyl or alkenyl[s] having about 8 to about 30 carbon atoms;

$R^{10}$ and $R^{11}$ are independently hydrogen or alkyl having up to about 4 carbon atoms; and $R^{12}$ is alkyl having up to about 4 carbon atoms; and [the salts of (III) and (IV) where $R^{12}$ on the nitrogenatom is hydrogen.]

*$A^-$ is an anion;*

*a linear or branched chain saturated or unsaturated fatty acid having from about 12 to about 22 carbon atoms;*

*a tertiary amine salt having the formula:*

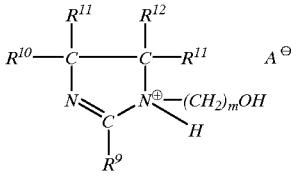

*(VII)*

*or*

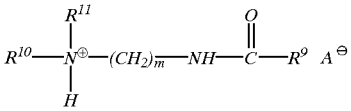

*(VIII)*

*and a fatty acid ester having the formula:*

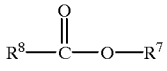

*wherein $R^7$ is a lower alkyl group or cyclo lower alkyl group and $R^8$ is a linear or branched chain, aliphatic saturated or unsaturated group having from about 11 to about 21 carbon atoms.*

8. The composition of any of claims 6 or 7 where said [tertiary amine, quaternizing agent and fatty acid are present in an amount of] *mixture contains* about 10 wt. % to about 80 wt. % of said quaternary ammonium compound, about 15 wt. % to about 70 wt. % of said *tertiary amine* salt, about 1 wt. % to about 70 wt. % of said ester and about 5 wt. % to about 70 wt. % of said fatty acid, *and* wherein the ratio of said quaternary ammonium compound to said *tertiary amine* salt, is from about 2:1 to about 1:2 on a weight basis.

9. The composition of any of claims 6 or 7 where said [tertiary amine, quaternizing agent and fatty acid are present in an amount so that said] mixture contains about 35 wt. % to about 55 wt. % of said quaternary ammonium compound, about 10 wt. % to about 30 wt. % of said *tertiary amine* salt, about 5 wt. % to about 25 wt. % of said ester and about 15 wt. % to about 35 wt. % of said fatty acid wherein the ratio of said quaternary ammonium compound to said *tertiary amine* salt, is from about 2:1 to about 1:2 on a weight basis.

10. The mixture of claim 6 where said quaternary ammonium compound is *a compound of formula* (I) and wherein at least one of said R, $R^1$ and $R^2$ groups is a branched chain or linear, aliphatic saturated or unsaturated hydrocarbon group having from about 12 to about 22 carbon atoms and the balance, if any, of said R, $R^1$ and $R^2$ groups is a lower alkyl group.

11. The mixture of claim [9] *10* where $A^-$ is a lower alkyl sulfate group and where *said at least one of said* R, $R^1$ and $R^2$ is [said] *a saturated* hydrocarbon group [it is saturated].

12. A fabric softening article of manufacture comprising a fabric softening amount of any of the mixtures of claims 6 or 7, operatively associated with a substrate that will release said mixture to a fabric under fabric softening conditions.

13. The article of claim 12 where said substrate is a fabric.

14. The article of claim 12 where said substrate is a porous polymeric material.

15. A fabric cleaning composition comprising a detergent in combination with a fabric softening amount of the mixtures of any of claims 6 or 7.

16. The composition of claim 15 where said detergent is a synthetic detergent.

17. The composition of claim 15 where said detergent is a soap.

* * * * *